United States Patent [19]
Barth et al.

[11] 3,992,388
[45] Nov. 16, 1976

[54] 4-(2-PYRIDYLAMIDOETHYL)PIPERIDINES

[75] Inventors: Wayne E. Barth, East Lyme; Donald E. Kuhla, Gales Ferry, both of Conn.

[73] Assignee: Pfizer Inc., New York, N.Y.

[22] Filed: Oct. 17, 1975

[21] Appl. No.: 623,351

Related U.S. Application Data

[62] Division of Ser. No. 504,826, Sept. 10, 1974, Pat. No. 3,933,830.

[52] U.S. Cl............ 260/293.69; 260/293.52; 260/293.56; 260/293.58; 260/295 R; 260/295 AM; 260/295.5 R; 260/295.5 A; 260/296 R; 424/267
[51] Int. Cl.².................................. C07D 213/56
[58] Field of Search.................... 260/293.69

[56] References Cited
UNITED STATES PATENTS
2,712,014    6/1955    Suter et al. .................. 260/293.69

*Primary Examiner*—Henry R. Jiles
*Assistant Examiner*—Robert T. Bond
*Attorney, Agent, or Firm*—Connolly and Hutz

[57] ABSTRACT

Disclosed herein is an improved process for the preparation of known hypoglycemic piperidinesulfamylureas of the structue

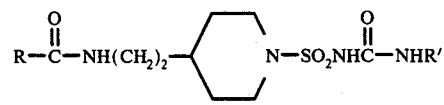

wherein R is selected from the group consisting of 3-(2-methoxy)pyridyl, 3-(2-ethoxy)pyridyl and 2-(4-chloro)pyridyl and R' is selected from the group consisting of bicyclo[2.2.1]hept-5-en-2-yl-endo-methyl, bicyclo[2.2.1]hept-2-yl-endo-methyl, 7-oxabicyclo[2.2.1]hept-2-yl-methyl, 1-adamantyl and cycloalkyl having from five to eight carbon atoms.

Said process comprises contacting 4-(2-pyridyl-amidoethyl) piperidine of the structue

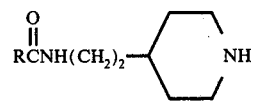

with substantially one equivalent of sulfamide thereby exclusively sulfonating the piperidine nitrogen atom. Said 4-(2-pyridylamidoethyl)piperidines from the corresponding 4-(2-pyridylamidoethyl) pyridines by selectively activating the more basic nitrogen atom of said pyridine compound either by N-alkylation or by contact with acid and then exclusively reducing the activated pyridine ring with either hydrogen alone or in combination with a metal hydride. Said 4-(2-pyridylamidoethyl)pyridines are produced by contacting 4-(2-aminoethyl)pyridine with a pyridyl acid chloride of the formula R(C=O)Cl. The piperidine sulfonamides produced by the process of the instant invention are converted to the desired hypoglycemic agent by methods well-known to those skilled in the art.

The 4-(2-pyridylamidoethyl)pyridines and piperidines of the instant invention are themselves novel compounds useful as intermediates in the synthesis of piperidine sulfamylurea hypoglycemic agents.

2 Claims, No Drawings

4-(2-PYRIDYLAMIDOETHYL)PIPERIDINES

CROSS-REFERENCE TO RELATED APPLICATIONS

This application is a divisional of application Ser. No. 504,826 filed Sept. 10, 1974 now U.S. Pat. No. 3,933,830.

The piperidinesulfamylurea hypoglycemic agents prepared by the process disclosed herein are themselves disclosed in the copending, commonly assigned application Ser. No. 305,594 filed Nov. 10, 1972, the disclosure of which is incorporated herein by reference, now U.S. Pat. No. 3,829,434.

BACKGROUND OF THE INVENTION

When administered orally, the piperidinesulfamylureas disclosed in the above-mentioned application function as hypoglycemic agents. Particularly useful are those compounds in which the piperidine ring is substituted in the 4-position with various 2-pyridylamidoethyl radicals. Because of their remarkable ability to reduce blood sugar levels with a minimum of side effects, these compounds are particularly useful in the treatment of diabetes mellitus and therefore, a safe, economic method for their production is highly desirable.

Previously, 2-aminoethylpyridine was reacted with phthalic anhydride to form N-[2-(4-pyridyl)-ethyl]phthalimide which was then reduced with hydrogen in the presence of an anhydrous acid and a catalyst to yield N-[2-(4-piperidyl)-ethyl]phthalimide. Said phthalimide was then reacted with sulfamide to produce 4-(2-phthalimidoethyl)-1-piperidine sulfonamide. The conversion of the aminoethyl function to the phthalimidoethyl function permits the sulfamide to react only with the piperidine nitrogen. To proceed further with the synthesis, the phthalimide must be cleaved to give the primary amine. Though many other reagents were tried, this reaction could be best effected with anhydrous hydrazine, a highly explosive compound which is extremely dangerous to use in commercial-scale syntheses. The product of the hydrazine reaction is 4-(2-amino-ethyl)-1-piperidine sulfonamide which was then contacted with an appropriate substituted pyridyl acid chloride to yield a 4-(2-pyridylamidoethyl)-1-piperidine sulfonamide which was then elaborated as outlined below to yield the desired hypoglycemic agent.

SUMMARY OF THE INVENTION

In accord with the present invention, known hypoglycemic agents of the structure

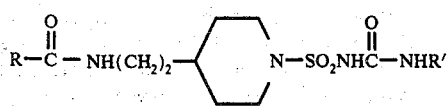

wherein R is selected from the group consisting of 3-(2-methoxy)pyridyl, 3-(2-ethoxy)pyridyl and 2-(4-chloro)pyridyl and R' is selected from the group consisting of bicyclo[2.2.1]hept-5-en-2-yl-endo-methyl, bicyclo[2.2.1]hept-2-yl-endo-methyl, 7-oxabicyclo[2.2.1]hept-2-yl-methyl, 1-adamantyl and cycloalkyl having from five to eight carbon atoms may be prepared by an improved process which comprises contacting a 4-(2-pyridylamidoethyl)piperidine of the structure

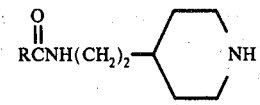

with a substantially equimolar portion of sulfamide at reflux temperatures until the reaction which produces exclusively the piperidine sulfonamide is substantially complete.

Said 4-(2-pyridylamidoethyl)piperidine is prepared from the corresponding 4-(2-pyridylamidoethyl)pyridine by selectively activating either by contact with acid or by N-alkylation, the more basic pyridine ring and subsequently reducing it with hydrogen either alone or in combination with a metal hydride.

Said 4-(2-pyridylamidoethyl)pyridines, 4-(2-pyridylamidoethyl)piperidines and their salts are themselves novel compounds and valuable intermediates. Particularly preferred are the 3-(2-methoxy)pyridyl compounds.

The present invention reduces the number of steps in the reaction sequence by two, eliminates the use of phthalic anhydride and the need for its subsequent removal by using a pyridyl acid chloride in its stead which not only protects the amine from sulfonation and thereby insures the addition of sulfamide at only the piperidyl nitrogen but also remains as a moiety in the desired molecule, eliminates the extremely hazardous use of anhydrous hydrazine and exclusively reduces the mono-substituted pyridine ring by a process of selective activation.

Particularly preferred is the preparation of the compound wherein R is 3-(2-methoxy)pyridyl and R' is bicyclo[2.2.1]hept-5-en-2-yl-endo-methyl.

DETAILED DESCRIPTION OF THE INVENTION

The process of this invention is novel in two particular aspects. First, various substituted pyridyl chlorides are used as blocking agents on the aliphatic amino group of 4-(2-aminoethyl)pyridine to prevent multiple sulfonation and, since said substituted pyridyl moieties constitute an element of the structure of the desired hypoglycemic agent, the need for their subsequent removal is obviated. Such is not the case with the process known in the art wherein phthalic anhydride, when used as a blocking agent, must be removed by contact with hazardous anhydrous hydrazine. Second, because of the difference in basicity of the two pyridine nitrogens in the various 4-(2-pyridylamidoethyl)pyridines of interest, the mono-substituted ring may be activated and reduced essentially exclusively to the desired (4-(2-pyridylamidoethyl)piperidine or piperidinium salt. Also, this difference in basicities causes sulfonation to take place exclusively at the piperidine nitrogen. In the present invention, exclusivity implies that the desired product was obtained in high yield and that no side products were formed which interfered with the recovery of the desired product.

Said 4-(2-pyridylamidoethyl)pyridines, 4-(2-pyridylamidoethyl) piperidines and their salts are themselves novel compounds and valuable intermediates.

In the preferred embodiment, 4-(2-aminoethyl)pyridine [L. E. Brady et al., Journal of Organic Chemistry, 26, 4784 (1961).] is first contacted with an approximately equimolar amount of a substituted pyridyl chloride selected from the group consisting of 2-methoxynicotinyl chloride, 2-ethoxynicotinyl chloride and 4-chloropicolinyl chloride in an appropriate reaction-inert solvent such as methylene chloride in the presence of a suitable base such as sodium carbonate in water at a temperature between about 0° and 40° C. until the reaction to form the desired product is substantially complete. Reaction-inert solvents are those which are substantially free of adverse effects on reactants and products under the conditions employed. Said product is then recovered from the reaction mixture and purified by the methods outlined below which are well-known to those skilled in the art of organic chemistry. Of particular interest as a product is 4-[2-(2-methoxynicotinamido)-ethyl]pyridine.

The various substituted pyridyl chlorides are prepared from the corresponding pyridine acids by contacting them with thionyl chloride in a suitable reaction-inert solvent such as methylene chloride at reflux temperatures until the formation of the desired acid chloride is substantially complete. 2-Methoxy and 2-ethoxy nicotinic acids are prepared by contacting 2-chloro-nicotinic acid [G. M. Badger et al., *Australian Journal of Chemistry*, 18, 1267 (1965).] with sodium methoxide or sodium ethoxide respectively in a reaction-inert solvent such as a lower alkanol at a temperature of about 90° to 130° C. in an autoclave until the reaction to form the desired product is substantially complete. 4-chloropicolinic acid may be prepared by the method of H. Meyer et al., *Chemische Berichte*, 61, 2210 (1928).

The next step in the synthetic process requires the selective reduction of the mono-substituted pyridine ring in said 4-(2-pyridylamidoethyl)pyridine prepared by the above-mentioned methods to form the desired 4-(2-pyridylamidoethyl)piperidine. It is known in the art [M. Freifelder, *Advances in Catalysis*, 14, 203–253 (1963).] that pyridine compounds may be activated and made more susceptible to reduction by the presence of an acid, by N-acylation or alkylation. Whenever two or more pyridine rings are present in the same compound, the problem is more complex because an equilibrium mixture of activated and non-activated species exists. It is known in the art that when a compound containing two identical pyridine rings is contacted with one equivalent of acid and hydrogenated, a pyridylpiperidine will be formed in preference to a dipiperidine [F. J. McCarthy et al., *Journal of the American Chemical Society*, 79, 472, (1957).]. The essentially exclusive activation and reduction of a pyridine ring in a compound containing two or more non-equivalent pyridine rings is unknown in the art. It has been found that, if the basicities of the nitrogen atoms in such compounds are sufficiently different and if only one equivalent of acid is employed, the acid will react essentially exclusively with the most basic nitrogen atom. The same exclusivity dependent upon different pyridine basicities generally exists in the case of N-alkylation or acylation. In the 4-(2-pyridylamidoethyl)-pyridines of interest, the $pK_b$ of the monosubstituted pyridine is approximately four pK units greater than that of the disubstituted one. Therefore, the monosubstituted ring can, be activation with an acid or by N-alkylation, be exclusively reduced to the desired piperidine.

The preferred process employs an acid rather than N-alkylation to activate the pyridine ring. In that process, a 4-(2-pyridylamidoethyl)pyridine at a concentration of about 10 to 30% by weight in a reaction-inert solvent such as a substantially anhydrous lower alkanol is contacted with approximately one equivalent of a substantially anhydrous mineral acid such as sulfuric acid, hydrogen chloride, hydrogen bromide, hydrogen iodide, anhydrous organic acids such as lower alkanoic and halogenated lower alkanoic acids and suitable Lewis acids such as aluminum trichloride and boron trifluoride etherate, and hydrogen and at a pressure of 25 to 75 psig. and a temperature of 15° to 40° C. in the presence of a noble metal catalyst until the reaction to form the 4-(2-pyridylamidoethyl)piperidinium salt is substantially complete. Noble metal catalysts as employed in the present invention include platinum, palladium, rhenium, rhodium and ruthenium, either of the supported or non-supported type, as well as the known catalytic compounds thereof such as the oxides, chlorides, etc. Examples of suitable catalyst supports include carbon, silica, keiselguhr, alumina and barium sulfate. The catalyst may be preformed or formed in situ by the pre-reduction of an appropriate salt or oxide of the catalytic compound. Platinum oxide is the preferred catalyst in this reaction. An aqueous acid may often be substituted for substantially anhydrous acid for the sake of convenience in the reduction reactions of the present invention. Dilution effect is important here. The mixture of a small volume of aqueous acid with a large volume of said substantially anhydrous reaction-inert solvent will itself frequently be subtantially anhydrous for the purposes of the present invention. The use of aqueous acid makes it unnecessary to dissolve an anhydrous acid which is usually a gas in the anhydrous solvent and then titrate the solution to determine its concentration. The use of aqueous acid is exemplified below. Sulfuric acid or hydrogen chloride are preferred as the acids, methanol as the solvent and about 40 to 60 psig. as the pressure range. The desired piperidine product may be recovered by removing the catalyst by filtration, concentrating the reaction mixture to an oil in vacuo, extracting said oil with an appropriate aqueous base, and drying said oil with a suitable desiccant.

Alternatively, N-alkylation may be used to activate the monosubstituted pyridine ring for reduction. Particularly preferred as alkylating agents are benzyl bromide, benzyl iodide, α-bromo- and α-iodoxylenes, the α-bromo and α-iodonaphthalenes and the mono- and disubstituted derivatives thereof wherein said substituents are chosen from the group consisting of lower alkyl, lower alkoxy, phenyl and phenoxy. These are preferred over other N-alkyl moieties because they are removed from the pyridine ring in the process of the hydrogen reduction. Many other alkylating agents such as alkyl and cycloalkyl halides adequately activate the pyridine ring for reduction but these agents must be removed subsequent to reduction by a process such as the von Braun reaction which employs cyanogen bromide as a reagent. Because the use of these other alkylating agents necessitates an extra synthetic step, the use of said benzyl and related compounds is generally preferred.

The 4-(2-pyridylamidoethyl)pyridine at a concentration of about 2 to 5% by weight in a suitable reaction-inert solvent such as acetonitrile, chloroform, dioxane or tetrahydrofuran is contacted with approximately an equimolar amount of one of said suitable alkylating agents at reflux temperature until the reaction to form the desired pyridinium salt is substantially complete. On cooling the product precipitates. Said product may, if desired, be recrystallized directly from suitable solvents such as an approximately one-to-one mixture of a lower alkanol with a lower alkyl ether; it may also be used directly in the next synthetic step without purification.

Said pyridinium salt is subsequently dispersed in an appropriate reaction-inert solvent such as an anhydrous lower alkanol or ether at concentration of about 2 to 5% by weight and contacted with an approximately fourfold molar excess of a suitable metal hydride reducing agent such as sodium borohydride or sodium bis-(2-methoxyethoxy)aluminum hydride which is added in portions with stirring over about a ten minute period at a temperature of about 0° to 5° C. Lithium aluminum hydride may be employed as a reducing agent but should be used in a substantially equivalent amount to avoid reduction of the amide carbonyl function. After the addition of said reducing agent is complete, the temperature of the reaction mixture is allowed to rise to ambient and the mixture stirred until the reaction to form the tetrahydropyridine derivative is substantially complete. The reaction mixture is evaporated in vacuo and the resulting oil is partitioned between water and ether. The layers are then separated, the aqueous layer extracted again with ether and the combined organic layers are treated with a drying agent, filtered and concentrated again in vacuo to yield the crude tetrahydropyridine derivative which is used directly in the next reaction. The preferred metal hydride is sodium borohydride and the preferred solvent is anhydrous methanol.

Said crude tetrahydropyridine derivative is then dispersed in a suitable reaction-inert solvent such as an anhydrous lower alkanol at a concentration of about 2 to 10% by weight along with an equivalent amount of mineral or organic acid such as hydrochloric, sulfuric or acetic acid and a catalytic amount of a noble metal catalyst. The preferred mode employs palladium on carbon as the catalyst, anhydrous methanol as the solvent and hydrogen chloride as the acid. Said reaction mixture is then contacted with hydrogen at a pressure up to about 400 psig. and a temperature of about 40° to 75° C. until the reaction to form the desired 4-(2-pyridylamidoethyl)piperidine is substantially complete. The catalyst is then separated by filtration, washed with said solvent, the wash and filtrate combined and then concentrated in vacuo to yield the desired product in crude form. Said crude product may be purified by suspending it in an appropriate water-immiscible solvent such as diethyl ether, washing with aqueous base, drying said organic layer and concentrating it in vacuo to yield the desired product in a substantially pure form.

Said 4-(2-pyridylamidoethyl)piperidines may be sulfonated exclusively at the piperidyl nitrogen by dispersing them in a reaction-inert solvent such as pyridine at concentration of about 20 to 60% by weight contacting them with an approximately equimolar amount of sulfamide and refluxing the reaction mixture until the formation of the desired 4-(2-pyridylamidoethyl)-piperidine sulfonamide is substantially complete. Here, as is the case with activation and reduction, the exclusivity is dependent upon differing nitrogen basicities. The product may be isolated in pure form by pouring the reaction mixture into ice water from which the product precipitates. Separation by filtration followed by recrystallization from a suitable solvent such as a lower alkanol yields the desired product in substantially pure form.

Said piperidine sulfonamides may be converted to the desired hypoglycemic agents by contacting them in approximately equimolar amounts with the diphenylcarbamoyl chloride derivative of the appropriate bicyclic amine in a suitable solvent such as dimethylformamide in the presence of sodium hydride in mineral oil until the reaction to form the desired hypoglycemic agent is substantially complete. In the case in which cycloalkyl or 1-adamantyl derivatives are desired, the piperidine sulfonamide is contacted with the appropriate alicyclic isocyanate. Said hypoglycemic agents are usually administered as the sodium salt. Conversion to said sodium salt may be effected by treatment of said hypoglycemic agents dissolved in methanol with sodium methoxide in methanol.

EXAMPLE 1

4-[2-(2-Methoxynicotinamido)-ethyl]pyridine

A 3 liter, three neck, round bottom flask equipped with a mechanical stirrer, reflux condenser and dropping funnel was charged with 4-(2-aminoethyl)pyridine (61.0 g., 0.5 mole) in 50 ml. of methylene chloride. Sodium carbonate (124.0 g., 1.0 mole) in water was added in one portion, and with stirring the heterogeneous reaction mixture was cooled in an ice-bath. 2-Methoxynicotinyl chloride (86 g., 0.5 mole) in methylene chloride (500 ml.) was added drop-wise and the mixture was allowed to warm to room temperature as vigorous stirring was continued for 2 hours. At this point the organic layer was removed and the aqueous layer extracted twice with 100 ml. portions of methylene chloride. The combined organic layers were then extracted three times with cold, dilute (0.5N) sodium hydroxide. The organic layer was dried over sodium sulfate, filtered and concentrated in vacuo to a yellow oil, which solidified upon standing, affording 97 g. (0.37 mmole, 75%) of product. Recrystallization from cyclohexane gave the analytical sample, a white crystalline solid, m.p. 84°–97°.

Analysis Calc. for $C_{14}H_{15}O_2N_3$: C, 65.35%; H, 5.88%; N, 16.33%. Found: C, 65.04%; H, 5.9%; N, 16.04%.

In similar fashion, the 3-(2-ethoxy)pyridyl and the 2-(4-chloro)pyridyl analogs of the title compound may be prepared.

EXAMPLE 2

4-[2-(2-Methoxynicotinamido)ethyl]piperidine

This Example illustrates the use of anhydrous acid to activate the pyridine compound and reduce it to the desired piperidine compound.

4-[2-(2-methoxynicotinamido)ethyl]pyridine obtained from Example 1 (25.7 g., 0.1 mole) in anhydrous methanol (150 ml.) was placed in a Parr hydrogenation bottle (800 ml. capacity). Exactly one equivalent of aqueous hydrochloric acid (17 ml. of 0.589N acid) and 1.0 g. of platinum oxide were added and the mixture hydrogenated at 80 p.s.i. until hydrogen uptake was complete (about 2 hrs.) The catalyst was removed by filtration and the reaction mixture concentrated in vacuo to a yellow, viscous oil. This oil was dissolved in chloroform (800 ml.) and extracted with sodium hydroxide (4x with 200 ml. portions of 2N NaOH). The organic layer was dried over sodium sulfate, filtered, and evaporated to dryness to give 27 g (ca. 0.1 mole, 100%) of product, a light yellow oil. This material was used directly in the next step of the reaction. An analytical sample of the picrate was prepared for reference. Crude 4-[2-(2-methoxynicotinamido)ethyl] (270 mg., 1 mole) in ethanol was treated with an excess of ethanolic picric acid solution. A yellow solid immediately precipitated. This solid was recrystallized twice from methanol to give the analytical sample, 4-[2-(2-methoxynicotinamido)ethyl]-piperidine picrate, m.p. 204°–206°.

Anal. Calc. for $C_{20}H_{24}O_9N_6$: C, 48.78; H, 4.91; N, 17.07%. Found: C, 48.44; H, 5.15; N, 17.13%.

In similar fashion, the 3-(2-ethoxy)pyridyl and the 2-(4-chloro)pyridyl analogs of the title compound may be prepared.

EXAMPLE 3

1-Benzyl-4-[2-(2-Methoxynicotinamido)-ethyl]-Pyridinium Bromide

This Example and the following illustrate activation by N-alkylation and the subsequent selective reduction to the desired piperidine compound.

A 250 ml. round bottom flask was charged with 4-[2-(2-methoxynicotinamido)-ethyl]pyridine obtained from Example 1 (2.57 g., 0.01 mole), acetonitrile (50 ml.) and benzyl bromide (1.71 g., 0.01 mole). The flask was equipped with a reflux condenser and the clear solution was refluxed for 2 hours. At this point, the reaction mixture was cooled and diethylether was added until the solution began to turn cloudy. A crystalline solid began to precipitate slowly. After standing overnight the product was removed by filtration to afford 3.64 g. (0.0085 mole, 85%) of product, a hard white crystalline solid, m.p. 125°–128°. Recrystallization from isopropanol/diethylether (1:1) gave the analytical sample, m.p. 126°–128°.

Anal. Calc. for $C_{21}H_{22}O_2N_3Br \cdot H_2O$: C, 56.50%; H, 5.42; N, 9.12%. Found: C, 56.34%; H, 5.43; N, 9.41%.

In similar fashion, the 3-(2-ethoxy)pyridyl and the 2-(4-chloro)pyridyl analogs of the title compound may be prepared.

EXAMPLE 4

4-[2-(2-Methoxynicotinamido)-ethyl]Piperidine

This Example illustrates the reduction of the activated compound obtained in Example 3.

A 250 ml. round-bottom flask was charged with 1-benzyl-4-[2-(2-methoxynicotinamido)-ethyl]-pyridinium bromide obtained from Example 3 (4.46 g., 0.01 mole) and 150 ml. of anhydrous methanol. The reaction mixture was cooled to 0°–5° C. and sodium borohydride (1.5 g., 0.04 mole) was added in portions over a 10 minute period. The reaction mixture was stirred at room temperature for an additional 30 minutes at which point it was concentrated to dryness in vacuo. The resulting viscous yellow oil was partitioned between diethylether/water, the layers were separated and the aqueous layer was extracted with an additional 100 ml. ether. The combined organic layers were dried over sodium sulfate, filtered and concentrated in vacuo to give ca. 3.55 g. (0.01 mole, ca. 100%) of crude product, a light yellow oil. The above crude product was hydrogenated directly at this point. Said crude product (ca. 3.55 g. 0.01 moles) was dissolved in 80 ml. of absolute methanol. To this solution was added 250 mg. of 10% Pd/C catalyst and one equivalent of aqueous HCl (10 ml. of a 1.00N solution). The reaction mixture was hydrogenated under 300 p.s.i. hydrogen at 50° for 6 hours in a high pressure hydrogenation apparatus. After removal from the hydrogenator the reaction mixture was filtered and the catalyst washed with methanol (100 ml.). Concentration of the clear filtrate afforded a yellow oil. This oil was suspended in diethylether (500 ml.) and washed with dilute sodium hydroxide (100 ml. of 1N NaOH) and finally water. The organic layer was dried over sodium sulfate, filtered, and concentrated in vacuo to give ca. 2.0 g. (0.0076 mole 76%) of product, a light yellow oil. An analytical sample of the picrate of 4-[2-(2-methoxynicotinamido)-ethyl]piperidine was prepared for reference purpose. Crude free base (270 mg., 1 mole) in methanol was treated with an excess of ethanolic picric acid solution. A yellow solid immediately precipitated. This solid was recrystallized twice from methanol to give the analytical sample, m.p. 204°–206°.

Anal. Calc. for $C_{20}H_{24}O_9N_6$: C, 48.78; H, 4.91; N, 17.08%. Found: C, 48.44; H, 5.15; N, 17.13%.

In similar fashion, the 3-(2-ethoxy)pyridyl and the 2-(4-chloro)pyridyl analogs of the title compound may be prepared.

EXAMPLE 5

4-[2-(2-Methoxynicotinamido)-ethyl]-1-Piperidine Sulfonamide

Crude 4-[2-methoxynicotinamido)-ethyl]piperidine as obtained from either Example 2 or 4 26.5 g., 0.1 mole) was dissolved in pyridine (40 ml.), sulfamide (9.6 g., 0.1 mole) added, and the mixture refluxed for one hour. The yellow solution was poured into ice water and the white solid which precipitated was removed by filtration to give 24.0 g. (0.07 mole, 70%) of product, m.p. 179°–181°. Recrystallization from methanol afforded the analytical sample, m.p. 180°–182°.

In similar fashion, the 3-(2-ethoxy)pyridyl and the 2-(4-chloro)pyridyl analogs of the title compound may be prepared.

EXAMPLE 6

1-(Bicyclo[2.2.1]-hept-5-en-2-yl-endomethyl)-3-{4-[2-(2-methoxynicotinamido)-ethyl]-piperidinosulfonyl}-urea-Sodium Salt.

Preparation A

To each of two 12 l. round-bottomed flasks under nitrogen was charged 1232 g. (10.0 moles) of bicyclo[2.2.1]hept-5-en-2-yl-methylamine which was available from Aldrich as a mixture of exo and endo isomers. After cooling to 10° C., triethylamine (1214 g., 12 moles) was added to each flask. A mild exotherm occurred during which the reaction mixture temperature rose to 35° C. Then, ethanol (5 l.) was added followed by diphenylcarbamoyl chloride (2317 g., 10.0 moles). Again the temperature rose to 35° C. The thick yellow suspension was stirred at room temperature for half an hour and at reflux for 19 hours.

The resultant solutions were then combined and distilled in vacuo until 4.3 l. had been collected. The crystalline slurry was then cooled and filtered. After the solids had been slurried in water (11 l.) and filtered, they were dissolved in boiling isopropanol (8 l.), filtered and allowed to crystallize to yield N-(N',N'-diphenylcarbamoyl)-bicyclo[2.2.1]hept-5-en-2-yl-endomethylamine m.p. 127°–128° (2432 g., 45% yield).

Preparation B

4-[2-(2-methoxynicotinamido)-ethyl]-1-piperidine sulfonamide (210.0 g., 0.613 moles) and the product of Preparation A (200.0 g., 0.629 moles) were added to dimethylformamide (1.480 l.) in a 50 l. round-bottomed flask under nitrogen sodium hydride (26.7 g.) which is available from Ventron as a 56.6% by weight solution in mineral oil was added and the reaction mixture heated on a steam bath at 70° C. for 1 hour. The reaction mixture was cooled and poured into ether (3 l.). The ether was washed twice with water (2 l. each) and the water backwashed with ether (1 l.). The aqueous layer was separated and acidified with 200 ml. of 6N HCl and then extracted three times with ethyl acetate (1 l. each). The extracts were dried with magnesium sulfate, treated with charcoal and stripped in vacuo to yield an oil. The oil was dissolved in 500 ml. of hot acetonitrile filtered and diluted with ether (11.5 l.). The cloudy solution yielded 100 g. of impure product. The mother liquors were concentrated to an oil and along with the impure product dissolved in a minimal amount of benzene-ethylacetate-acetic acid (67:33:1) and the solution put on a 3 kg. silica gel column (48" X 4"Q). Using the same solvent as the eluent and taking 1 liter cuts, the pure product was found in cuts 8 through 15. These fractions were combined, stripped to an oil (33 g.), dissolved in hot acetonitrile and crystallized by the addition of four parts ether. The product (33 g.) was separated by filtration and found to be substantially pure by thin layer chromatography.

Preparation C

A 2 liter round-bottomed flask was charged with the product of Preparation B (120 g., 0.244 moles) and absolute methanol (700 ml.). The solution was cooled to −20° C. and sodium methoxide (13.20 g., 0.244 moles) was added in three separate portions over a ten minute period. The reaction mixture was stirred for 20 minutes while allowing the temperature to rise to + 5° C. The resulting solution was filtered and treated with ether (8 l.). After a 1.5 hour granulation period, additional ether (1 l.) was added. The solution was filtered to obtain a solid residue (120 g. wet weight) m.p. 207°–209° C. This material was dissolved in 700 ml. of refluxing methanol and concentrated to 500 ml. After treatment with charcoal, the solution was diluted with ether (2 l.) and allowed to crystallize. Additional ether (1 l.) was added after granulation was complete. The product was filtered and washed with ether (1 l.) to give the title compound as white needle crystals, m.p. 210°–212° C. (111.0 g., 89% yield).

In similar fashion, one may also prepare the analogous compounds wherein R and R' are

| R | R' |
| --- | --- |
| 3-(2-ethoxy)pyridyl | bicyclo[2.2.1]hept-5-en-2-yl-endo-methyl |
| 2-(4-chloro)pyridyl | bicyclo[2.2.1]hept-5-en-2-yl-endo-methyl |
| 3-(2-methoxy)pyridyl | bicyclo[2.2.2]hept-2-yl-endo-methyl |
| 3-(2-ethoxy)pyridyl | bicyclo[2.2.2]hept-2-yl-endo-methyl |
| 2-(4-chloro)pyridyl | bicyclo[2.2.2]hept-2-yl-endo-methyl |
| 3-(2-methoxy)pyridyl | 7-oxabicyclo[2.2.1]hept-2-yl-methyl |
| 3-(2-ethoxy)pyridyl | 7-oxabicyclo[2.2.1]hept-2-yl-methyl |
| 2-(4-chloro)pyridyl | 7-oxabicyclo[2.2.1]hept-2-yl-methyl |

The cycloalkyl and 1-adamantyl derivatives of interest may also be prepared by omitting Preparation A and employing an appropriate cycloalkyl isocyanate or 1-adamantyl isocyanate in Preparation B instead of the diphenylcarbamoyl chloride derivative.

What is claimed is:
1. A 4-(2-pyridylamidoethyl)piperidine of the formula

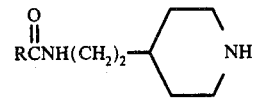

wherein R is selected from the group consisting of 3-(2-methoxy)pyridyl, 3-(2-ethoxy)pyridyl and 2-(4-chloro)pyridyl.

2. The piperidine of claim 1 wherein R is 3-(2-methoxy)pyridyl.

* * * * *